(12) United States Patent
Murayama et al.

(10) Patent No.: US 10,591,473 B2
(45) Date of Patent: Mar. 17, 2020

(54) ANTIGEN DETECTION METHOD USING SANDWICH IMMUNOASSAY METHOD

(71) Applicant: KONICA MINOLTA, INC., Chiyoda-ku, Tokyo (JP)

(72) Inventors: Takanori Murayama, Kunitachi (JP); Atsuo Iwashita, Machida (JP)

(73) Assignee: KONICA MINOLTA, INC., Tokyo (JP)

( * ) Notice: Subject to any disclaimer, the term of this patent is extended or adjusted under 35 U.S.C. 154(b) by 360 days.

(21) Appl. No.: 15/032,261

(22) PCT Filed: Oct. 22, 2014

(86) PCT No.: PCT/JP2014/078071
§ 371 (c)(1),
(2) Date: Apr. 26, 2016

(87) PCT Pub. No.: WO2015/064441
PCT Pub. Date: May 7, 2015

(65) Prior Publication Data
US 2016/0245803 A1 Aug. 25, 2016

(30) Foreign Application Priority Data

Oct. 31, 2013 (JP) ................................ 2013-227268

(51) Int. Cl.
*B01L 3/00* (2006.01)
*G01N 33/543* (2006.01)
(Continued)

(52) U.S. Cl.
CPC ..... *G01N 33/54366* (2013.01); *G01N 21/648* (2013.01); *G01N 21/77* (2013.01);
(Continued)

(58) Field of Classification Search
None
See application file for complete search history.

(56) References Cited

U.S. PATENT DOCUMENTS

2006/0263818 A1* 11/2006 Scherer ............... B01L 3/50273
435/6.11
2006/0292641 A1  12/2006 Nakanishi et al.
(Continued)

FOREIGN PATENT DOCUMENTS

JP   2006053094 A   2/2006
JP   2006226841 A   8/2006
(Continued)

OTHER PUBLICATIONS

International Search Report (ISR) dated Jan. 27, 2015 issued in International Application No. PCT/JP2014/078071.
(Continued)

*Primary Examiner* — Rebecca L Martinez
(74) *Attorney, Agent, or Firm* — Holtz, Holtz & Volek PC

(57) ABSTRACT

An antigen detection method using sandwich immunoassay includes a first reaction step of preparing a sensor chip, which includes a fine flow channel in which a reaction zone having an antigen-capturing antibody immobilized thereon is arranged, a liquid discharge/suction section and a liquid-mixing section, and subsequently feeding thereto a sample liquid so as to allow the antigen-capturing antibody to capture a target; and a second reaction step of allowing a labeling liquid containing a labeling antibody to flow into the fine flow channel so as to label the target. In the antigen detection method, the labeling liquid does not reach the liquid-mixing section. According to the antigen detection method, the accuracy and the repeatability of the target measurement can be improved.

19 Claims, 5 Drawing Sheets

(51) Int. Cl.
  *G01N 21/64* (2006.01)
  *G01N 21/77* (2006.01)
(52) U.S. Cl.
  CPC ..... *G01N 33/543* (2013.01); *G01N 33/54393* (2013.01); *B01L 3/502* (2013.01); *G01N 2021/7786* (2013.01)

(56) References Cited

U.S. PATENT DOCUMENTS

| | | |
|---|---|---|
| 2008/0019866 A1 | 1/2008 | Paek et al. |
| 2012/0156800 A1* | 6/2012 | Aoki .................... G01N 21/553 436/180 |
| 2014/0099236 A1 | 4/2014 | Yamamoto et al. |

FOREIGN PATENT DOCUMENTS

| | | |
|---|---|---|
| JP | 2007010341 A | 1/2007 |
| JP | 2010243419 A | 10/2010 |
| JP | 2013185967 A | 9/2013 |
| WO | 2006062312 A1 | 6/2006 |
| WO | 2011027851 A1 | 3/2011 |
| WO | 2012153723 A1 | 11/2012 |

OTHER PUBLICATIONS

Extended European Search Report (EESR) dated Apr. 5, 2017, issued in counterpart European Application No. 14857184.7.
Japanese Office Action dated Jun. 26, 2018 (and an English language translation thereof) issued in counterpart Japanese Application No. 2015-544943.

* cited by examiner

[Fig. 1]
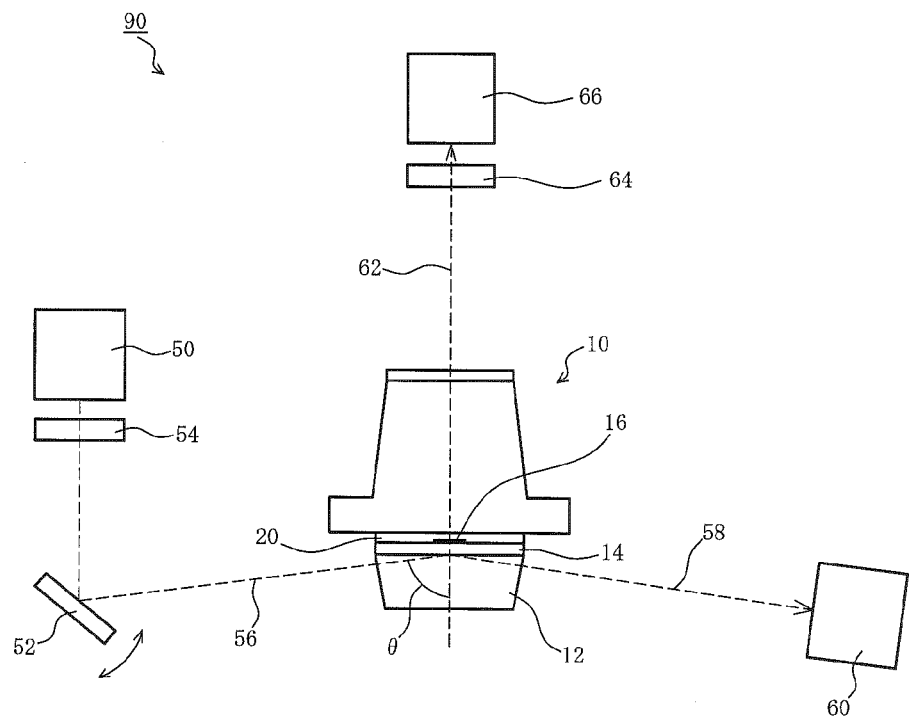
[Fig. 2]
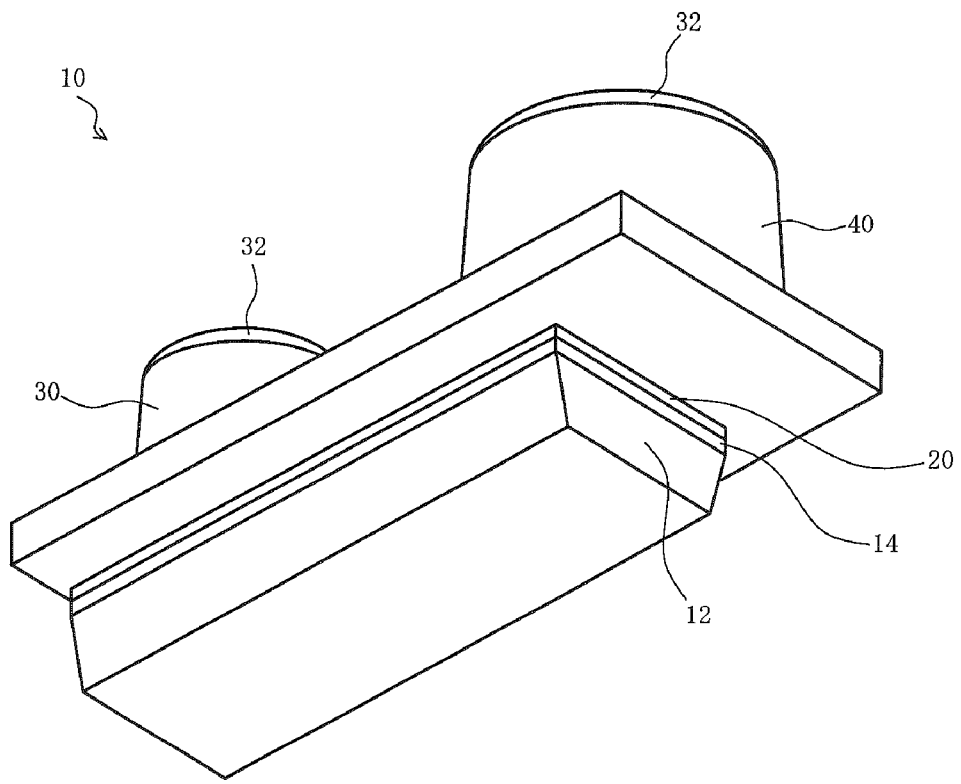

[Fig. 3]
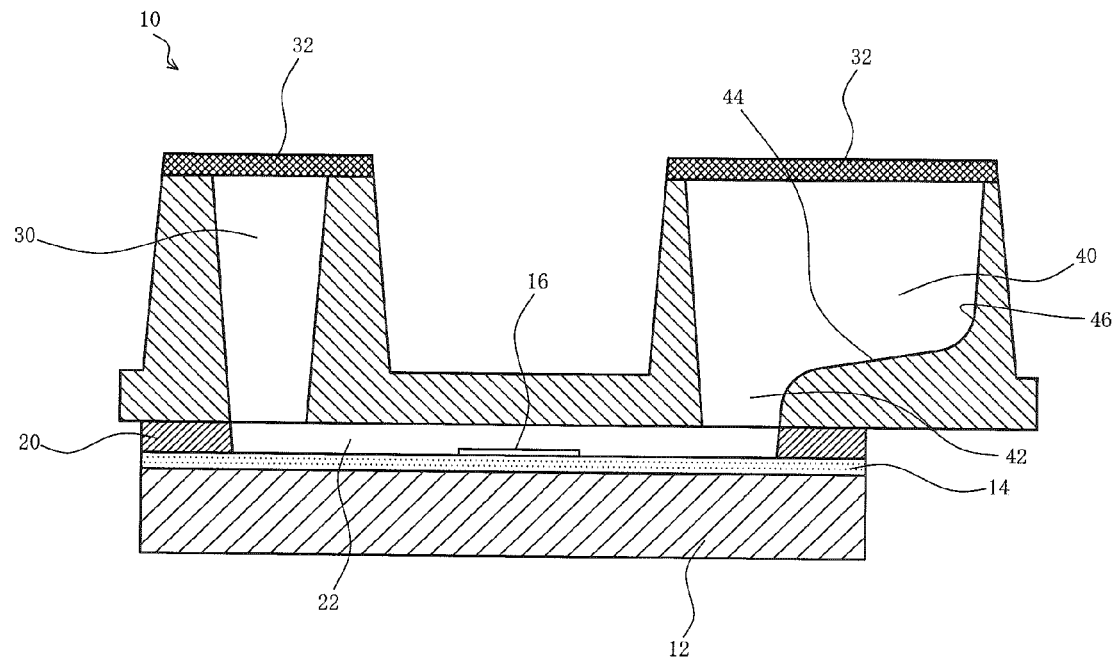
[Fig. 4]
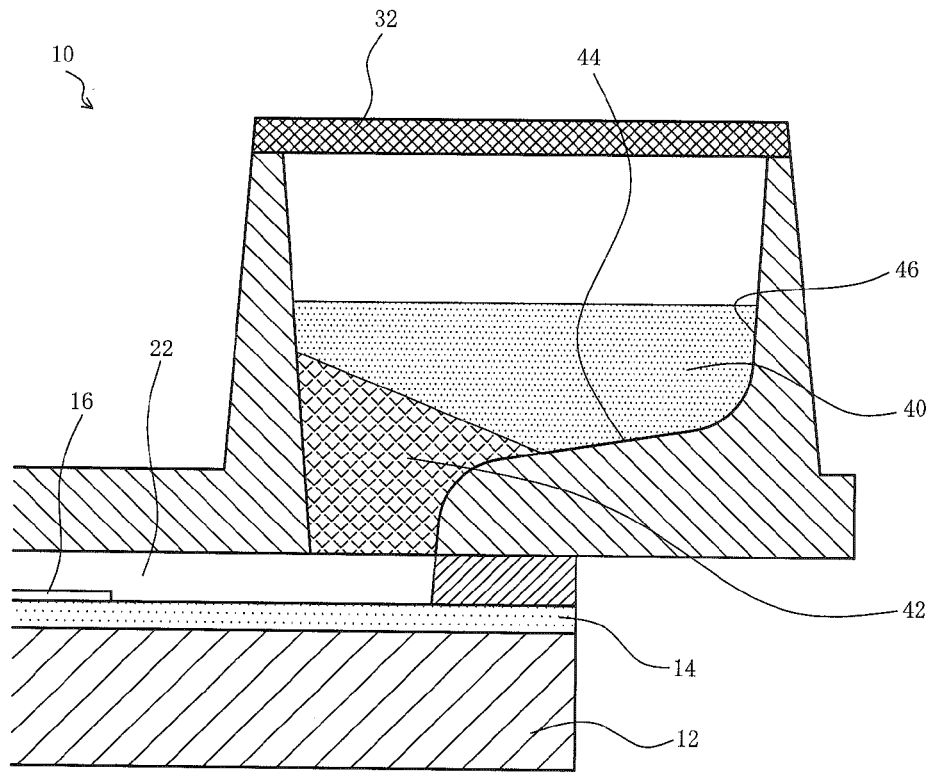

[Fig. 5]
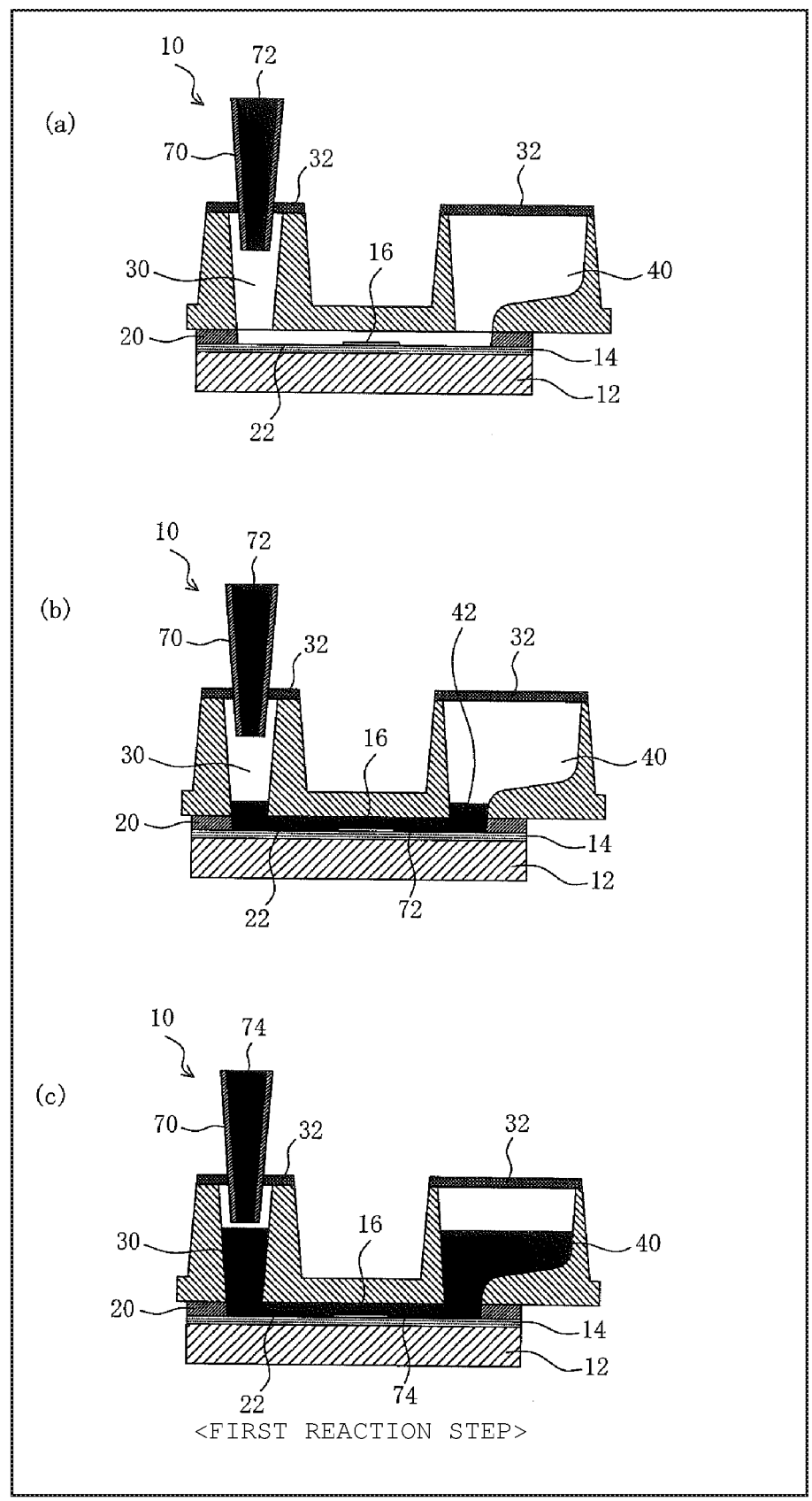

[Fig. 6]
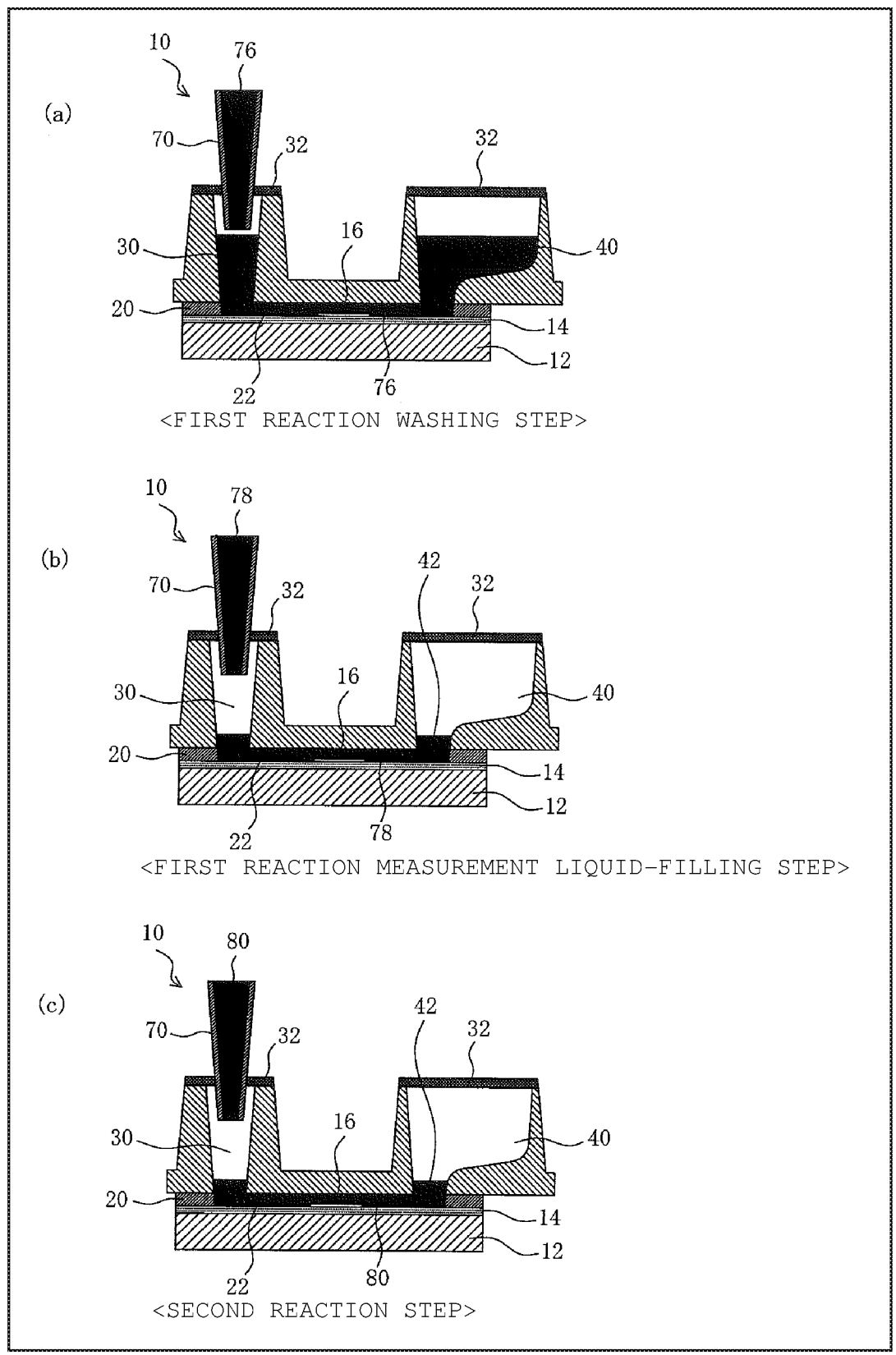

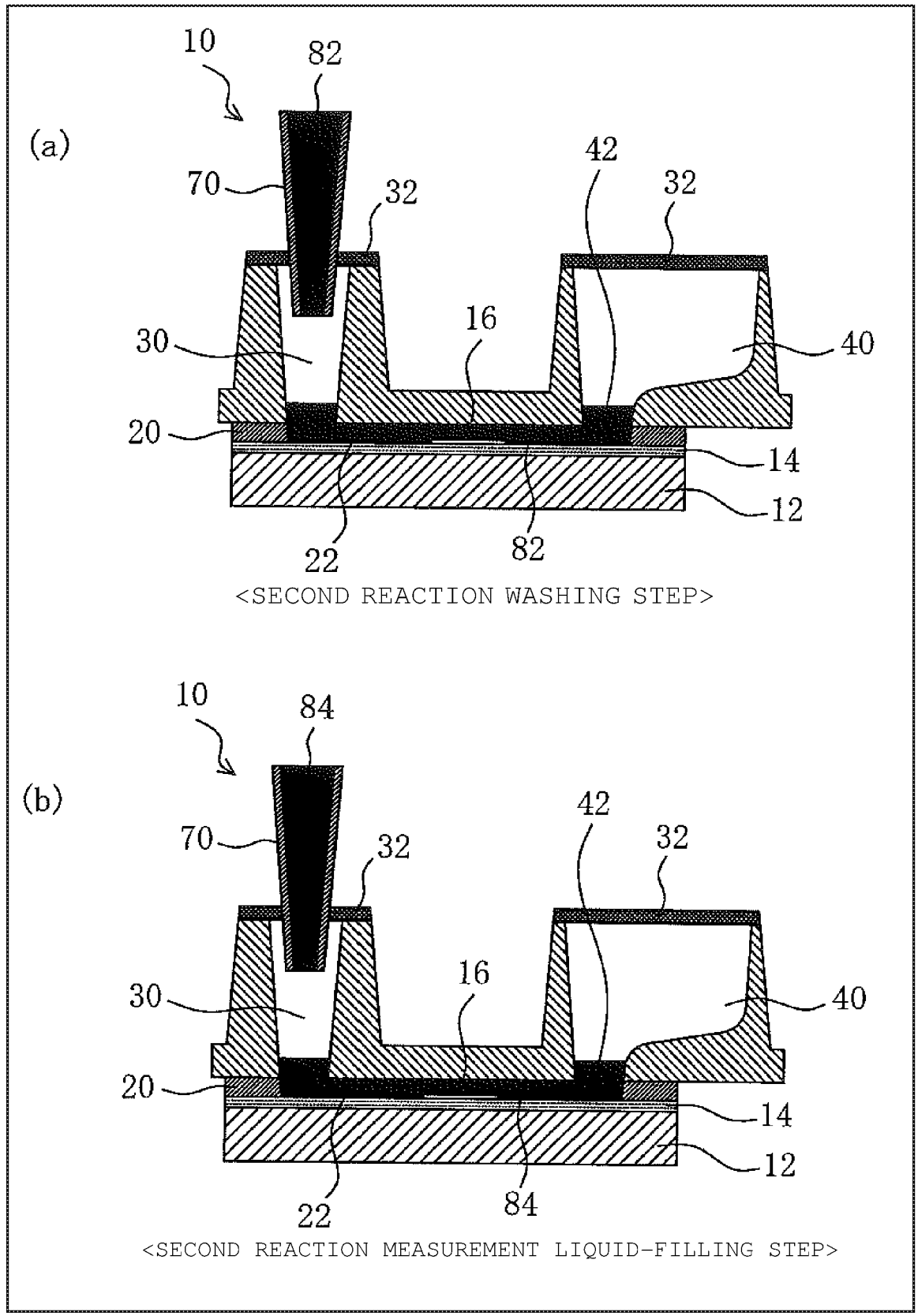

ANTIGEN DETECTION METHOD USING SANDWICH IMMUNOASSAY METHOD

TECHNICAL FIELD

The present invention relates to an antigen detection method using sandwich immunoassay by which a target antigen can be detected with good accuracy.

BACKGROUND ART

Biochemical tests utilize a biochemical reaction such as antigen-antibody reaction, and take place using a sensor chip on which a fine flow channel is formed. In such a sensor chip, for example, an antigen-capturing antibody is immobilized on the inner surface in the middle of a fine flow channel. The fine flow channel is supplied with a target antigen-containing sample liquid, thereby allowing the antigen contained in the sample liquid and the antigen-capturing antibody to bind with each other.

After the fine flow channel is supplied with the sample liquid, the presence or absence of binding of the antigen to the antigen-capturing antibody and the like are determined, and the amount thereof and the like are measured. In the determination and measurement, the fine flow channel is supplied with liquids other than the sample liquid, such as a washing liquid and a labeling liquid (fluorescent labeling liquid). Then, surface plasmon-field enhanced fluorescence spectroscopy (SPFS) takes place.

In many cases, the liquids are discharged and suctioned using a pipette via a liquid discharge/suction section arranged on the upstream side of the fine flow channel. In addition, a liquid-mixing section is arranged on the downstream side of the fine flow channel. The fine flow channel enables to, for example, generate turbulence in the liquids, thereby ensuring that the antigen is bound to the antigen-capturing antibody and the like (for example, Patent Document 1).

CITATION LIST

Patent Document

[Patent Document 1] JP-A-2013-185967

SUMMARY OF THE INVENTION

Problems to be Solved by the Invention

By the way in such a biochemical reaction, it is known that measurement cannot be performed accurately due to the effects from non-specific adsorption caused by impurities (e.g., proteins other than the target antigen) in the sample liquid, a labeling antibody in the labeling liquid and the like. Particularly, low-concentration sample liquids are largely affected by such non-specific adsorption. This may lead to a reduction in the reliability of the measured values.

In a biochemical reaction using a sensor chip, it is difficult to completely recover a liquid remaining in the flow path (e.g., liquid discharge/suction section, fine flow channel and liquid-mixing section). The recovery is even more difficult particularly in a sensor chip having such a complex shape that has a liquid-mixing section (liquid pool).

Furthermore, the amount of a liquid remaining in the flow path is not always constant and is highly likely to be different for each measurement. Such difference in the amount of the residual liquid for each measurement makes the amount of non-specific adsorption be different for each measurement. This leads to a problem, namely the difference in the amount of non-specific adsorption for each measurement adversely affects the repeatability particularly in the measurement of a target contained in a low-concentration sample liquid.

In view of the above-described circumstances, an object of the present invention is to provide an antigen detection method using sandwich immunoassay, which can reduce the effects of non-specific adsorption, and thereby particularly can improve the accuracy of measuring a target contained in a low-concentration sample liquid and also can improve the repeatability of the target measurement.

Technical Solution

In order to realize at least one of the above-described objects, the antigen detection method using sandwich immunoassay according to the present invention has the following features.

That is, the antigen detection method using sandwich immunoassay, comprising at least:

the first reaction step of preparing a sensor chip, which comprises at least a reaction zone where an antigen-capturing antibody is immobilized in the middle of a fine flow channel, a liquid discharge/suction section on the upstream side of the fine flow channel and a liquid-mixing section on the downstream side of the fine flow channel, and subsequently feeding a sample liquid containing a target antigen to the reaction zone of the sensor chip so as to allow the antigen-capturing antibody to capture the target;

the second reaction step of allowing a labeling liquid containing a labeling antibody to flow into the fine flow channel so as to label the target captured by the antigen-capturing antibody, after the first reaction step; and the signal measurement step of measuring a signal obtained from the labeling antibody used for labeling the target in the second reaction step, wherein, in the first reaction step, when the sample liquid containing the target antigen is fed to the reaction zone, the sample liquid is fed until the sample liquid reaches the liquid-mixing section arranged on the downstream side of the fine flow channel, and in the second reaction step, when the labeling liquid is fed to the reaction zone where the target antigen has been captured by the antigen-capturing antibody, the labeling liquid is fed in such a manner that the labeling liquid does not reach the liquid-mixing section arranged on the downstream side of the fine flow channel.

Advantageous Effects of Invention

According to the present invention, there is provided a an antigen detection method using sandwich immunoassay, in which in the second reaction step the amount of the labeling liquid to be fed to the reaction zone is adjusted so that the labeling liquid does not reach the liquid-mixing section, thereby reducing the effects of non-specific adsorption. This particularly leads to improvement of the accuracy of measuring a target contained in a low-concentration sample liquid and also leads to improvement of the repeatability of the target measurement.

BRIEF DESCRIPTION OF THE DRAWINGS

FIG. 1 shows an SPFS apparatus provided with a sensor chip for performing the antigen detection method of the present invention.

FIG. 2 shows the sensor chip for performing the antigen detection method of the present invention.

FIG. 3 is a vertical cross-sectional view of the sensor chip shown in FIG. 2.

FIG. 4 is an enlarged view showing a main part of the liquid-mixing section across the vertical cross-sectional view of the sensor chip shown in FIG. 3.

FIG. 5 is a process chart for explaining the antigen detection method of the present invention.

FIG. 6 is a process chart for explaining the antigen detection method of the present invention.

FIG. 7 is a process chart for explaining the antigen detection method of the present invention.

DESCRIPTION OF THE EMBODIMENTS

An embodiment of the present invention will now be described in more detail referring to the drawings.

The present invention relates to an antigen detection method using sandwich immunoassay by which a target antigen can be detected with good accuracy.

In the antigen detection method using sandwich immunoassay according to the present invention, the following method can be employed as one of working examples.

That is, the antigen detection method using sandwich immunoassay comprises at least:

the first reaction step of preparing a sensor chip, which comprises at least a reaction zone where an antigen-capturing antibody is immobilized in the middle of a fine flow channel, a liquid discharge/suction section on the upstream side of the fine flow channel and a liquid-mixing section on the downstream side of the fine flow channel, and subsequently feeding a sample liquid containing a target antigen to the reaction zone of the sensor chip so as to allow the antigen-capturing antibody to capture the target;

the second reaction step of allowing a labeling liquid containing a labeling antibody to flow into the fine flow channel so as to label the target captured by the antigen-capturing antibody, after the first reaction step; and the signal measurement step of measuring a signal obtained from the labeling antibody used for labeling the target in the second reaction step, wherein, in the first reaction step, when the sample liquid containing the target antigen is fed to the reaction zone, the sample liquid is fed until the sample liquid reaches the liquid-mixing section arranged on the downstream side of the fine flow channel, and in the second reaction step, when the labeling liquid is fed to the reaction zone where the target antigen has been captured by the antigen-capturing antibody, the labeling liquid is fed in such a manner that the labeling liquid does not reach the liquid-mixing section arranged on the downstream side of the fine flow channel.

In this antigen detection method, the labeling liquid is not fed to the liquid-mixing section in the second reaction step. This does not lead to problems which arise when the labeling liquid is fed to the liquid-mixing section. Namely, this antigen detection method does not include (1) a problem that impurities contained in the sample liquid, which remain in the liquid-mixing section in the first reaction step, flow from the liquid-mixing section back to the reaction zone along with the labeling liquid to cause non-specific adsorption. Further, this antigen detection method also does not include (2) a problem in: a case that the washing liquid is fed to the liquid-mixing section in the subsequent second reaction washing step; and/or a case that the measurement liquid is fed to the liquid-mixing section in the second reaction measurement liquid-filling step. Here, the problem in the case(s) are that the labeling antibody in the labeling liquid, which remains in the liquid-mixing section in the second reaction step, flows from the liquid-mixing section back to the reaction zone along with a washing liquid and/or the measurement liquid to cause non-specific adsorption.

Particularly regarding the above (1), the washing liquid is delivered to the liquid-mixing section in the first reaction washing step followed by the first reaction step. This allows to the amount of (non-specifically adsorbing) impurities remaining therein be small. However, even such a small amount of impurities has a large effect on the measurement results in those measurement systems such as SPFS that are capable of measuring a small amount of a target with high sensitivity.

Reducing the effects of non-specific adsorption of impurities and labeling antibody in the above-described manner prevents a reduction in the reliability due to false detection in the antigen detection and the like. This particularly leads to improvement of the accuracy of measuring a target contained in a low-concentration sample liquid, and also leads to improvement of the repeatability of the target measurement.

Furthermore, since the labeling liquid is not fed to the liquid-mixing section, the amount of the labeling liquid used in the second reaction step can be reduced as compared to a case where the labeling liquid is fed to the liquid-mixing section. This enables to reduce the cost required for the labeling liquid and also to shorten the time required for feeding the labeling liquid.

The antigen detection method using sandwich immunoassay according to the present invention preferably comprises the second reaction washing step of washing the reaction zone with a washing liquid after the second reaction step, wherein in the second reaction washing step, the washing liquid is fed in such a manner that the washing liquid does not reach the liquid-mixing section arranged on the downstream side of the fine flow channel.

Not allowing the washing liquid to reach the liquid-mixing section prevents the impurities in the sample liquid that remain in the liquid-mixing section in the first reaction step, from flowing from the liquid-mixing section back to the reaction zone along with the washing liquid to cause non-specific adsorption.

The washing liquid contains a surfactant and the like, which are capable of detaching and removing substances non-specifically adsorbing to the flow path. Therefore, the possibility of causing the non-specific adsorption anew by the flow of the washing liquid is low. However, not feeding the washing liquid to the liquid-mixing section can fundamentally eliminate such possibility.

Such further reduction of the effects of non-specific adsorption particularly improves the accuracy of measuring a target contained in a low-concentration sample liquid, and also improves the repeatability of the target measurement.

Furthermore, not feeding the washing liquid to the liquid-mixing section allows the amount of the washing liquid to be reduced as compared to cases where the washing liquid is fed to the liquid-mixing section. This enables to reduce the cost required for the washing liquid, and also to shorten the time required for feeding the washing liquid.

Further, the antigen detection method using sandwich immunoassay according to the present invention preferably comprises the second reaction measurement liquid-filling step of filling the reaction zone with a measurement liquid after the second reaction washing step, wherein in the second reaction measurement liquid-filling step, the measurement liquid is fed in such a manner that the measurement liquid does not reach the liquid-mixing section arranged on the downstream side of the fine flow channel.

Not allowing the measurement liquid to reach the liquid-mixing section prevents the impurities in the sample liquid that remain in the liquid-mixing section in the first reaction step, from flowing from the liquid-mixing section back to the reaction zone along with the measurement liquid. This leads to further reduction of the effects of non-specific adsorption, thereby particularly allowing the accuracy of measuring a target contained in a low-concentration sample liquid to be improved and also allowing the repeatability of the target measurement to be improved.

Furthermore, not feeding the measurement liquid to the liquid-mixing section allows the amount of the measurement liquid to be reduced as compared to cases where the measurement liquid is fed to the liquid-mixing section. This enables to reduce the cost required for the measurement liquid, and also to shorten the time required for feeding the measurement liquid.

Further, the antigen detection method using sandwich immunoassay according to the present invention preferably comprises:

the second reaction washing step of washing the reaction zone with a washing liquid after the second reaction step; and the second reaction measurement liquid-filling step of filling the reaction zone with a measurement liquid after the second reaction washing step, wherein in the second reaction measurement liquid-filling step, the measurement liquid is fed in such a manner that the measurement liquid does not reach the liquid-mixing section arranged on the downstream side of the fine flow channel.

Not allowing the measurement liquid to reach the liquid-mixing section allows the effects of non-specific adsorption to be reduced as above described. This particularly leads to improvement of the accuracy of measuring a target contained in a low-concentration sample liquid, and also leads to improvement of the repeatability.

Furthermore, not feeding the measurement liquid to the liquid-mixing section allows the amount of the measurement liquid to be reduced as compared to cases where the measurement liquid is fed to the liquid-mixing section. This enables to reduce the cost required for the measurement liquid, and also to shorten the time required for feeding the measurement liquid.

In the antigen detection method using sandwich immunoassay according to the present invention, the above-described sample liquid, labeling liquid, washing liquid and measurement liquid are preferably fed via the liquid discharge/suction section in a reciprocating manner using a pipette.

Using a pipette is preferable from the viewpoint that the liquids can be fed simply and accurately in a reciprocating manner.

Further, in the antigen detection method using sandwich immunoassay according to the present invention, the above-described sample liquid, labeling liquid, washing liquid and measurement liquid are each preferably fed using the pipette up to a prescribed location by adjusting the amounts thereof.

Changing the feed location by adjusting the amount of each liquid ensures that the liquids are fed to the respective prescribed locations, thereby reducing the effects of non-specific adsorption. This particularly leads to improvement of the accuracy of measuring a target contained in a low-concentration sample liquid, and also leads to improvement of the repeatability and reproducibility of the target measurement.

Hereinafter, an SPFS apparatus provided with a sensor chip for performing the antigen detection method of the present invention and the antigen detection method using sandwich immunoassay according to the present invention will be described in detail.

First, an SPFS apparatus provided with a sensor chip for performing the antigen detection method of the present invention will be described. An SPFS apparatus is capable of performing antigen detection and the like by surface plasmon-field enhanced fluorescence spectroscopy (SPFS).

<SPFS Apparatus 90>

As shown in FIG. 1, in an SPFS apparatus 90 provided with a sensor chip 10 for performing the antigen detection method of the present invention, the sensor chip 10 comprises at least: a dielectric member 12; a metal thin film 14 formed on the upper surface of the dielectric member 12; and a fine flow channel-constituting member 20 arranged on the metal thin film 14.

In the sensor chip 10, as shown in FIG. 2, the fine flow channel-constituting member 20 forms a fine flow channel 22 on the metal thin film 14, and a liquid discharge/suction section 30 and a liquid-mixing section 40 are arranged on the upstream and downstream sides of the fine flow channel 22, respectively.

The upper surfaces of the liquid discharge/suction section 30 and the liquid-mixing section 40 are each sealed with a hermetic seal 32. Further, the upper surfaces are configured so that upon the use of the SPFS apparatus 90, the hermetic seal 32 can be pierced through with the tip of a pipette 70, whereby a liquid can be fed to the fine flow channel 22.

As for the material of the metal thin film 14 of the sensor chip 10, the metal thin film 14 comprises preferably at least one metal selected from the group consisting of gold, silver, aluminum, copper and platinum, more preferably gold, still more preferably an alloy of these metals. These metals are suitable for the metal thin film. 14 from the viewpoint that the metals are stable against oxidation and allow a large electric field enhancement by compression wave (surface plasmon).

Examples of a method for forming the metal thin film 14 include sputtering, vapor deposition (e.g., resistance heating vapor deposition or electron beam vapor deposition), electrolytic plating and electroless plating. Thereamong, sputtering and vapor deposition are preferred in the viewpoint that these methods allow the thin film-forming conditions to be easily adjusted.

The thickness of the metal thin film 14 is preferably in a range of 5 to 500 nm when the metal thin film 14 is made of gold, silver, aluminum, copper, platinum or an alloy of these metals.

From the viewpoint of electric field-enhancing effect, the thickness of the metal thin film 14 is more preferably in a range of 20 to 70 nm (gold), 20 to 70 nm (silver), 10 to 50 nm (aluminum), 20 to 70 nm (copper), 20 to 70 nm (platinum) or 10 to 70 nm (an alloy of these metals).

The thickness of the metal thin film 14 in the above-described range allows compression waves (surface plasmon) to be easily generated, and is therefore preferred. Further, the size (longitudinal×lateral) of the metal thin film 14 is not particularly restricted as long as the metal thin film 14 is formed at least between the dielectric member 12 and a reaction zone 16.

The metal thin film 14 is preferably formed in a linear form from one end to the other end of the dielectric member 12, at least on a part of the upper surface of the dielectric member 12. This allows the metal thin film 14 to be simply formed at a uniform thickness.

Meanwhile, as the dielectric member 12, a variety of optically transparent inorganic substances as well as natural or synthetic polymers can be used. From the viewpoints of chemical stability, production stability and optical transparency, the dielectric member 12 preferably contains silicon dioxide ($SiO_2$) or titanium dioxide ($TiO_2$).

The shape of the dielectric member 12 is not restricted to a hexahedral shape (truncated quadrangular pyramid) having a substantially trapezoidal cross-section as shown in FIG. 2, and may be, for example, a pyramidal shape such as a quadrangular pyramid, a cone, a triangular pyramid or a polygonal pyramid, or a truncated pyramidal shape. With the dielectric member 12 having a truncated quadrangular pyramidal shape, the height of the sensor chip 10 can be reduced and this can contribute to a size reduction of the SPFS apparatus 90.

Further, immobilizing the fine flow channel-constituting member 20 on the metal thin film 14 is preferably performed by using an adhesive, a matching oil, a transparent adhesive sheet or the like that has the same optical refractive index as the dielectric member 12.

The SPFS apparatus 90 comprises a light source 50 and a light-receiving means 60 on the side of the dielectric member 12 of the sensor chip 10 with the above-described structure. The light source 50 irradiates an excitation light 56 that enters the dielectric member 12 and travels toward the metal thin film 14. The light-receiving means 60 receives a reflected light 58 that is irradiated from the light source 50 and reflected by the metal thin film 14.

The excitation light 56 irradiated from the light source 50 is preferably a laser light. Suitable is an LD laser having a wavelength of 200 to 900 nm and an output of 0.001 to 1,000 mW or a semiconductor laser having a wavelength of 230 to 800 nm and an output of 0.01 to 100 mW.

The excitation light 56 irradiated from the light source 50 is preferably polarized by a polarizing plate 54. The thus polarized excitation light 56 is preferably irradiated to the metal thin film 14 via a mirror 52. However, not using the polarizing plate 54 and the mirror 52 causes no functional problems in the apparatus. Therefore, the polarizing plate 54 and the mirror 52 may be optionally selected and arranged in accordance with the size and structure of the apparatus.

Meanwhile, on the side of the fine flow channel-constituting member 20 of the sensor chip 10, a light-detecting means 66 is arranged, which receives fluorescence 62 generated in the reaction zone 16.

As the light-detecting means 66, an ultrahigh-sensitivity photomultiplier tube or a CCD image sensor capable of performing multipoint measurement is preferably used.

Between the fine flow channel-constituting member 20 of the sensor chip 10 and the light-detecting means 66, a wavelength selection function member 64 is preferably provided, which is configured so as to select only the fluorescence 62 among lights.

As the wavelength selection function member 64, an optical filter, a cut filter or the like may be used. Examples of the optical filter include neutral density (ND) filters and diaphragm lenses. Examples of the cut filter include filters, such as interference filters and color filters, which remove a variety of noise lights such as ambient light (illumination light outside the apparatus), excitation light (transmitted component of the excitation light), stray light (scattering components of the excitation light at various spots), scattering plasmon light (scattered light that is originated from the excitation light and generated due to the effect of a substance adhering to the surface of the sensor chip 10) and intrinsic fluorescence of an enzyme fluorescent substrate.

In the use of the SPFS apparatus 90 with the above-described structure, first, an antigen-capturing antibody which specifically adsorbs a target antigen is immobilized in advance on the reaction zone 16 on the metal thin film 14 of the sensor chip 10. In this state, a sample liquid 74 containing the target antigen is allowed to flow in the fine flow channel 22, thereby allowing the antigen-capturing antibody to capture the target antigen (first reaction).

Examples of the sample liquid 74 containing the target antigen include blood, serum, plasma, urine, nasal fluid, saliva, feces and body cavity fluids (e.g., spinal fluid, ascitic fluid and pleural effusion).

Examples of the target antigen include nucleic acids (such as DNAs, RNAs, polynucleotides, oligonucleotides and PNAs (peptide nucleic acids), which may be single-stranded or double-stranded; nucleosides; nucleotides; and modified molecules thereof), proteins (such as polypeptides and oligopeptides), amino acids (including modified amino acids), saccharides (such as oligosaccharides, polysaccharides and sugar chains), lipids, and modified molecules and complexes thereof. Specifically, the target antigen may be, but not particularly limited to, a carcinoembryonic antigen such as AFP (α-fetoprotein), a tumor marker, a signal transducer, a hormone or the like.

After allowing the antigen-capturing antibody to capture the target antigen, the inside of the fine flow channel 22 is washed with a washing liquid 76, and a labeling liquid 80 which contains a labeling antibody to be captured by the target antigen is allowed to flow in the fine flow channel 22. This leads to a state where the target antigen captured on the antigen-capturing antibody is labeled with the labeling antibody (second reaction).

The labeling antibody that labels the target antigen is preferably a fluorescent substance that is excited by irradiation with the prescribed excitation light 56 or by utilization of electric field effect and that emits the fluorescence 62. It is noted here that the term "fluorescence 62" used herein encompasses various light emissions such as phosphorescence.

After discharging the labeling liquid 80, the inside of the fine flow channel 22 is washed with a washing liquid 82, and this time, the fine flow channel 22 is filled with a measurement liquid 84. In this state, the excitation light 56 is irradiated from the light source 50 into the dielectric member 12, and then this excitation light 56 enters the metal thin film 14 at a specific angle (resonance angle θ). This operation can generate a compression wave (surface plasmon) on the metal thin film 14.

When a compression wave (surface plasmon) is generated on the metal thin film 14, the excitation light 56 and the electron oscillation in the metal thin film 14 are coupled. This coupling causes modification of the signal of the reflected light 58 (reduction of the light intensity). Therefore in order to generate a compression wave, the positions where the signal of the reflected light 58 received by the light-receiving means 60 is modified (the light intensity is reduced) may be appropriately determined.

For the purpose of adjusting the resonance angle θ, the SPFS apparatus 90 may also comprise, for example, an angle-changing section (not shown) and a computer (not shown) used for processing the information input to the light-detecting means 66. The angle-changing section (not shown) preferably synchronizes the light-receiving means 60 and the light source 50 for determination of the attenuated total reflection (ATR) condition using a servomotor; is capable of changing the angle in a range of 45° to 85°; and has a resolution of not less than 0.01°.

Due to the thus generated compression wave (surface plasmon), the fluorescent substance (labeling antibody) in the reaction zone 16 on the metal thin film 14 is efficiently excited, as a result of which the intensity of the fluorescence 62 emitted from the fluorescent substance is increased. This enhanced fluorescence 62 is collected using the light-detecting means 66 via the wavelength selection function member 64, whereby the target antigen of an extremely small amount and/or an extremely low concentration can be detected.

The washing liquids and measurement liquid herein are not particularly restricted as long as the washing liquids and measurement liquid do not adversely affect the respective steps of sandwich immunoassay. In this embodiment, the same buffer is used in the washing liquids and measurement liquid.

Examples of the buffer preferably used include a phosphate buffer, a Tris buffer, a citrate buffer, a borate buffer or a carbonate buffer. In order to improve the washing effect, a surfactant-containing buffer can be used. For example, a 0.02% polyoxyethylene sorbitan monolaurate (trade name: Tween-20)-containing phosphate buffer (pH 7.4) can be preferably used.

In the SPFS apparatus 90 of the present invention that has the above-described constitution, the amount of each liquid to be fed to the reaction zone 16 is adjusted when the above-described sensor chip 10 is used, and thereby reducing the effects of non-specific adsorption. This particularly leads to improvement of the accuracy of measuring a target contained in the low-concentration sample liquid 74, and also leads to improvement of the repeatability of the target measurement.

Hereinafter, the antigen detection method using sandwich immunoassay according to the present invention will be described in detail.

<Antigen Detection Method Using Sandwich Immunoassay>

In the antigen detection method using sandwich immunoassay according to the present invention, the sensor chip 10 shown in FIGS. 2 and 3 is used.

As described above, the sensor chip 10 comprises the liquid discharge/suction section 30 and the liquid-mixing section 40, which are arranged on the upstream and downstream sides of the fine flow channel 22, respectively. Further, the fine flow channel 22 comprises the reaction zone 16 in the middle thereof. In this reaction zone 16, an antigen-capturing antibody is immobilized. The antigen-capturing antibody has been immobilized in advance on the metal thin film 14 in the middle of the fine flow channel 22, in a state of being protected with a moisturizer (reagent). The sensor chip 10 is used after washing this moisturizer (reagent) with a washing liquid 72.

The hermetic seal 32 is pasted to the upper end of the liquid discharge/suction section 30 arranged on the upstream side of the fine flow channel 22. When using the sensor chip 10, the hermetic seal 32 is pierced through with the tip of the pipette 70, and then a liquid is fed to the fine flow channel 22. Accordingly, the diameter of the opening of the liquid discharge/suction section 30 is preferably set to be larger than the outer diameter of the tip of the pipette 70 to be used.

In this embodiment, the below-described sample liquid, labeling liquid, washing liquids and measurement liquid are fed via the liquid discharge/suction section 30 in a reciprocating manner using the pipette 70. Using the pipette 70 is preferable form the viewpoint that the liquids can be fed in a simple and accurate manner.

Meanwhile, the liquid-mixing section 40 arranged on the downstream side of the fine flow channel 22 has such a special form as shown in FIGS. 3 and 4. This form generates turbulence in the liquid-mixing section 40 and allows an antigen-antibody reaction to occur in a favorable manner when the sample liquid 74 containing a target antigen is fed to the antigen-capturing antibody immobilized on the reaction zone 16. This is important for improvement of the detection accuracy particularly in the detection of a rare antigen contained in the sample liquid 74 at a low concentration and the like.

The form of the liquid-mixing section 40 shown in FIGS. 3 and 4 is merely one embodiment and the form is not particularly restricted. In this form, the liquid-mixing section 40 is formed by a gently-sloping surface 44 and a vertical surface 46 that is arranged in an erected manner in continuation from the sloping surface 44, such that a favorable turbulence is generated when a liquid is fed until the liquid reaches the liquid-mixing section 40.

The fine flow channel 22 and the liquid-mixing section 40 have a connection part 42 therebetween, and are in communication with each other through this connection part 42. The connection part 42 has a structure in which influx of a liquid does not cause any turbulence.

The antigen detection method that uses the sensor chip 10 comprising such liquid-mixing section 40 is performed by the following steps.

First, as shown in FIG. 5(*a*), the sensor chip 10 with unopened hermetic seals 32 is prepared and the hermetic seal 32 on the side of the liquid discharge/suction section 30 is pierced with the tip of the pipette 70.

Then, as shown in FIG. 5 (*b*), the pipette 70 feeds the washing liquid 72 into the fine flow channel 22. This washing liquid 72 is fed for the purpose of removing the moisturizer (reagent) protecting the antigen-capturing antibody on the reaction zone 16. In this process, the washing liquid 72 does not have to be fed until the washing liquid 72 reaches the liquid-mixing section 40, and may be fed up to the connection part 42. In the feeding of the washing liquid 72 into the fine flow channel 22 using the pipette 70, the washing liquid 72 is fed in a reciprocating manner via the liquid discharge/suction section 30.

Next, the washing liquid 72 is suctioned using the pipette 70 to empty the fine flow channel 22. Then as shown in FIG. 5(*c*), the sample liquid 74 containing a target antigen is fed to the reaction zone 16 via the liquid discharge/suction section 30 using the pipette 70, thereby allowing the antigen-capturing antibody on the reaction zone 16 to capture the target antigen (first reaction step).

In this process, the sample liquid 74 is fed until the sample liquid reaches the liquid-mixing section 40 such that an antigen-antibody reaction takes place in a favorable manner in the reaction zone 16. By feeding the sample liquid 74 in a reciprocating manner for plural times using the pipette 70, turbulence is generated in the liquid-mixing section 40. This enables the antigen-capturing antibody in the reaction zone 16 on the fine flow channel 22 to favorably capture the target antigen.

Subsequently, the sample liquid 74 is suctioned using the pipette 70 to empty the fine flow channel 22. Then as shown in FIG. 6(*a*), the washing liquid 76 is fed to the reaction zone 16 via the liquid discharge/suction section 30 using the pipette 70 (first reaction washing step).

In this process, by feeding the washing liquid 76 in a reciprocating manner for plural times using the pipette 70 until the washing liquid reaches the liquid-mixing section 40, non-specifically adsorbed substances that remain in the fine flow channel 22, liquid-mixing section 40, connection part 42 and the like can be washed.

Subsequently, the washing liquid 76 is suctioned using the pipette 70 to empty the fine flow channel 22. Then as shown in FIG. 6 (b), the measurement liquid 78 is fed to the fine flow channel 22 via the liquid discharge/suction section 30 using the pipette 70 to fill the reaction zone 16 with the measurement liquid 78. In this process, the measurement liquid 78 is preferably kept from flowing beyond the connection part 42 (first reaction measurement liquid-filling step).

Next, with the reaction zone 16 being filled with measurement liquid 78, the metal thin film 14 of the sensor chip 10 is irradiated with the excitation light 56 using the light source 50, and the resonance angle θ is scanned by adjusting the irradiation angle.

Further, in this condition, fluorescence in the reaction zone 16 is detected using the light-detecting means 66 to perform fluorescence measurement in blank state prior to the second reaction.

Subsequently, the measurement liquid 78 in the fine flow channel 22 is suctioned using the pipette 70 to empty the fine flow channel 22. Then as shown in FIG. 6(c), the labeling liquid 80 containing a labeling antibody is fed to the fine flow channel 22 via the liquid discharge/suction section 30 using the pipette 70 to fill the reaction zone 16 with the labeling liquid 80. This allows the target captured by the antigen-capturing antibody to be labeled with the labeling antibody (second reaction step).

In this process, the labeling liquid 80 requires to be fed in such a manner that the labeling liquid 80 flows only to the connection part 42 without reaching the liquid-mixing section 40. This inhibits backflow of impurities in the sample liquid 74 that may be remaining on the sloping surface 44 and the like of the liquid-mixing section 40; and prevents the labeling antibody in the labeling liquid 80 from remaining on the sloping surface 44 and the like of the liquid-mixing section 40 (namely in an embodiment where the washing liquid 82 and measurement liquid 84 are delivered to the liquid-mixing section 40 in a later step, backflow of the residual labeling antibody to the reaction zone 16 can be inhibited).

Here, considering only the inhibition of the backflow and the prevention of the labeling antibody from remaining as described above, the labeling liquid 80 may be fed in such a manner that the labeling liquid 80 flows only to the downstream end of the fine flow channel 22 or more restrictively, only to the reaction zone 16, without reaching even to the connection part 42. However, if the labeling liquid 80 is allowed to flow only to the downstream end of the fine flow channel 22 or kept in the reaction zone 16, air bubbles may remain in the fine flow channel 22. Therefore desirably, the labeling liquid 80 is intentionally allowed to reach the connection part 42.

Subsequently, the labeling liquid 80 is suctioned using the pipette 70 to empty the fine flow channel 22. Then as shown in FIG. 7(a), the washing liquid 82 is fed to the fine flow channel 22 via the liquid discharge/suction section 30 using the pipette 70 to fill the reaction zone 16 with the washing liquid 82. Then by the washing liquid 82 in a reciprocating manner for plural times using the pipette 70, the reaction zone 16 is washed (second reaction washing step).

In this process, the washing liquid 82 is allowed to flow only to the connection part 42 without reaching the liquid-mixing section 40.

Not allowing the washing liquid 82 to reach the liquid-mixing section 40 in this manner prevents the impurities in the sample liquid 74 that remain in the liquid-mixing section 40 in the first reaction step, from flowing from the liquid-mixing section 40 back to the reaction zone 16 along with the washing liquid 82 to cause non-specific adsorption.

The washing liquid 82 contains a surfactant and the like, which are capable of detaching and removing substances non-specifically adsorbing to the flow path. Therefore, the possibility of causing the non-specific adsorption anew by the washing liquid 82 is low. However, not feeding the washing liquid 82 to the liquid-mixing section 40 can fundamentally eliminated such possibility.

Such further reducing the effects of non-specific adsorption particularly improves the accuracy of measuring a target contained in the low-concentration sample liquid 74, and also improves the repeatability of the target measurement.

Furthermore, not feeding the washing liquid 82 to the liquid-mixing section 40 allows the amount of the washing liquid 82 to be reduced as compared to cases where the washing liquid 82 is fed to the liquid-mixing section 40. This enables to reduce the cost required for the washing liquid 82, and also to shorten the time required for feeding the washing liquid 82.

Subsequently, the washing liquid 82 is suctioned using the pipette 70 to empty the fine flow channel 22. Then as shown in FIG. 7 (b), the measurement liquid 84 is fed to the fine flow channel 22 via the liquid discharge/suction section 30 using the pipette 70 to fill the reaction zone 16 with the measurement liquid 84. In this process, the measurement liquid 84 is preferably allowed to flow only to the connection part 42 (second reaction measurement liquid-filling step).

Not allowing the measurement liquid 84 to reach the liquid-mixing section 40 prevents the impurities in the sample liquid 74 that remain in the liquid-mixing section 40 in the first reaction step from flowing, from the liquid-mixing section 40 back to the reaction zone 16 along with the measurement liquid 84. This leads to further reduction of the effects of non-specific adsorption, thereby particularly allowing the accuracy of measuring a target contained in the low-concentration sample liquid 74 to be improved and also allowing the repeatability of the target measurement to be improved.

Furthermore, not feeding the measurement liquid 84 to the liquid-mixing section 40 allows the amount of the measurement liquid 84 to be reduced as compared to cases where the measurement liquid 84 is fed to the liquid-mixing section 40. This enables to reduce the cost required for the measurement liquid 84, and also to shorten the time required for feeding the measurement liquid 84.

By performing the above-described steps, the preparation for the antigen detection performed by the SPFS apparatus 90 is completed.

Thereafter, in this state, the fluorescence 62 in the reaction zone 16 is measured using the light-detecting means 66, and then the value previously measured in a blank state is subtracted from the thus measured fluorescence value. By this operation, the true measurement value based on the target antigen is obtained with high accuracy.

As described above in the present antigen detection method, the amount of the labeling liquid 80 to be fed to the reaction zone 16 is adjusted so as to not allowing the labeling liquid 80 to reach the liquid-mixing section 40, particularly in the second reaction step. This leads to reduction of the effects of non-specific adsorption, thereby particularly improving the accuracy of measuring a target contained in a low-concentration sample liquid.

In the present antigen detection method, the sample liquid 74, the labeling liquid 80, the washing liquids 72, 76 and 82 and the measurement liquids 78 and 84 are fed using a pipette up to the respective prescribed positions by adjusting the amounts thereof.

Here, there is shown an exemplary case where the sensor chip 10 has a capacity of about 40 µl for the flow path (at least a part of the liquid discharge/suction section 30 and the fine flow channel 22)+the connection part 42, and has a capacity of about 350 µl for the flow path (at least a part of the liquid discharge/suction section 30 and the fine flow channel 22)+the connection part 42+the liquid-mixing section 40. In this case, the feeding amount up to the connection part 42 is suitably 25 µl to 40 µl, and is particularly suitably 33 µl. Further, the feeding amount up to the liquid-mixing section 40 is suitably 50 µl to 300 µl, and is particularly suitably 85 µl. By adjusting the feeding amounts to the above ranges or values, the liquids are fed to the respective positions described above.

Change the position to which the liquid is fed by adjusting the amount of each liquid allows the liquids to be certainly fed to the respective prescribed positions. This leads to the reduction of the effects of non-specific adsorption, thereby improving the accuracy of measuring a target contained in the low-concentration sample liquid 74 in particular, and also improving the repeatability of the target measurement.

Furthermore, since the operation of the pipette 70 is easy, anyone can certainly feed a liquid to a prescribed position.

As described above in the antigen detection method of the present invention, the labeling liquid 80 is not fed to the liquid-mixing section 40 in the second reaction step. This does not lead to problems which arise when the labeling liquid is fed to the liquid-mixing section. Namely, this antigen detection method does not include (1) a problem that impurities contained in the sample liquid 74, which remain in the liquid-mixing section 40 in the first reaction step, flow from the liquid-mixing section 40 back to the reaction zone 16 along with the labeling liquid 80 to cause non-specific adsorption. Further, this antigen detection method also does not include (2) a problem in: a case that the washing liquid 82 is fed to the liquid-mixing section 40 in the subsequent second reaction washing step; and/or a case that the measurement liquid 78 is fed to the liquid-mixing section 40 in the second reaction measurement liquid-filling step. Here, the problem in the case(s) are that the labeling antibody in the labeling liquid 80, which remains in the liquid-mixing section 40 in the second reaction step, flows from the liquid-mixing section 40 back to the reaction zone 16 along with a washing liquid 82 and/or the measurement liquid 84 to cause non-specific adsorption.

Particularly regarding the above (1), the washing liquid 76 is delivered to the liquid-mixing section 40 in the first reaction washing step followed by the first reaction step. This allows to the amount of (non-specifically adsorbing) impurities remaining therein be small. However, even such a small amount of impurities has a large effect on the measurement results in those measurement systems such as SPFS that are capable of measuring a small amount of a target with high sensitivity.

Reducing the effects of non-specific adsorption of impurities and labeling antibody in the above-described manner prevents a reduction in the reliability due to false detection in the antigen detection and the like. This particularly leads to improvement of the accuracy of measuring a target contained in the low-concentration sample liquid 74, and also leads to improvement of the repeatability of the target measurement.

Furthermore, since the labeling liquid 80 is not fed to the liquid-mixing section 40, the amount of the labeling liquid 80 used in the second reaction step can be reduced as compared to a case where the labeling liquid 80 is fed to the liquid-mixing section 40. This enables not only to reduce the cost required for the labeling liquid 80 and also to shorten the time required for feeding the labeling liquid 80.

Thus far, the antigen detection method using sandwich immunoassay according to the present invention has been described. However, the present invention is not restricted to the above-described embodiment. For example, the liquid-mixing section 40 and the connection part 42 may assume different forms and the washing liquids and measurement liquids may be handled as separate components. Furthermore, a variety of modifications, such as the use of a reciprocating pump (not shown) in place of the pipette 70 for feeding a liquid, can also be made within the scope of the object of the present invention.

DESCRIPTION OF SYMBOLS

10: Sensor chip
12: Dielectric member
14: Metal thin film
16: Reaction zone
20: Fine flow channel-constituting member
22: Fine flow channel
30: Liquid discharge/suction section
32: Hermetic seal
40: Liquid-mixing section
42: Connection part
44: Sloping surface
46: Vertical surface
50: Light source
52: Mirror
54: Polarizing plate
56: Excitation light
58: Reflected light
60: Light-receiving means
62: Fluorescence
64: Wavelength selection function member
66: Light-detecting means
70: Pipette
72: Washing liquid
74: Sample liquid
76: Washing liquid
78: Measurement liquid
80: Labeling liquid
82: Washing liquid
84: Measurement liquid
90: SPFS apparatus
$\theta$: Resonance angle

The invention claimed is:

1. An antigen detection method, using sandwich immunoassay, the antigen detection method comprising:
a first reaction step including, in a sensor chip which comprises a reaction zone where an antigen-capturing antibody is immobilized within a fine flow channel, a liquid discharge/suction section on an upstream side of the fine flow channel, and a liquid-mixing section on a downstream side of the fine flow channel, wherein the liquid-mixing section has a special form configured to generate turbulence in the liquid mixing section, feeding a sample liquid containing a target antigen into the fine flow channel to the reaction zone of the sensor chip so as to allow the antigen-capturing antibody to capture the target antigen;

a second reaction step including feeding a labeling liquid containing a labeling antibody into the fine flow channel to the reaction zone so as to label the target antigen captured by the antigen-capturing antibody, after the first reaction step; and a signal measurement step including measuring a signal obtained from the labeling antibody used to label the target antigen in the second reaction step, wherein:
in the first reaction step, when the sample liquid containing the target antigen is fed to the reaction zone, the sample liquid is fed, via the fine flow channel, until the sample liquid reaches the liquid-mixing section arranged on the downstream side of the fine flow channel, and in the second reaction step, when the labeling liquid is fed to the reaction zone where the target antigen has been captured by the antigen-capturing antibody, the labeling liquid is fed, via the fine flow channel, in such a manner that the labeling liquid does not reach the liquid-mixing section arranged on the downstream side of the fine flow channel.

2. The antigen detection method according to claim 1, further comprising:
a second reaction washing step including washing the reaction zone with a washing liquid after the second reaction step,
wherein in the second reaction washing step, the washing liquid is fed in such a manner that the washing liquid does not reach the liquid-mixing section arranged on the downstream side of the fine flow channel.

3. The antigen detection method according to claim 2, further comprising:
a second reaction measurement liquid-filling step including filling the reaction zone with a measurement liquid after the second reaction washing step,
wherein in the second reaction measurement liquid-filling step, the measurement liquid is fed in such a manner that the measurement liquid does not reach the liquid-mixing section arranged on the downstream side of the fine flow channel.

4. The antigen detection method according to claim 1, further comprising:
a second reaction washing step including washing the reaction zone with a washing liquid after the second reaction step; and
a second reaction measurement liquid-filling step including filling the reaction zone with a measurement liquid after the second reaction washing step,
wherein in the second reaction measurement liquid-filling step, the measurement liquid is fed in such a manner that the measurement liquid does not reach the liquid-mixing section arranged on the downstream side of the fine flow channel.

5. The antigen detection method according to claim 1, wherein the sample liquid, the labeling liquid, a washing liquid, and a measurement liquid are fed via the liquid discharge/suction section in a reciprocating manner using a pipette.

6. The antigen detection method according to claim 5, wherein the sample liquid, the labeling liquid, the washing liquid, and the measurement liquid are each fed using the pipette up to a prescribed position by adjusting amounts thereof.

7. The antigen detection method according to claim 2, wherein in the second reaction washing step, the washing liquid is fed via the fine flow channel.

8. The antigen detection method according to claim 3, wherein:
in the second reaction washing step, the washing liquid is fed via the fine flow channel, and
in the second reaction measurement liquid-filling step, the measurement liquid is fed via the fine flow channel.

9. The antigen detection method according to claim 4, wherein in the second reaction measurement liquid-filling step, the measurement liquid is fed via the fine flow channel.

10. The antigen detection method according to claim 3, wherein the sample liquid, the labeling liquid, the washing liquid, and the measurement liquid are fed via the liquid discharge/suction section in a reciprocating manner using a pipette.

11. The antigen detection method according to claim 10, wherein the sample liquid, the labeling liquid, the washing liquid, and the measurement liquid are each fed using the pipette up to a prescribed position by adjusting amounts thereof.

12. The antigen detection method according to claim 4, wherein the sample liquid, the labeling liquid, the washing liquid, and the measurement liquid are fed via the liquid discharge/suction section in a reciprocating manner using a pipette.

13. The antigen detection method according to claim 12, wherein the sample liquid, the labeling liquid, the washing liquid, and the measurement liquid are each fed using the pipette up to a prescribed position by adjusting amounts thereof.

14. The antigen detection method according to claim 1, further comprising:
a first reaction washing step including washing the reaction zone with a first washing liquid after the first reaction step and before the second reaction step,
wherein in the first reaction washing step, the first washing liquid is fed, via the fine flow channel, until the first washing liquid reaches the liquid-mixing section arranged on the downstream side of the fine flow channel.

15. The antigen detection method according to claim 14, further comprising:
a first reaction measurement liquid-filling step including filling the reaction zone with a first measurement liquid after the first reaction washing step and before the second reaction step;
wherein in the first reaction measurement liquid-filling step, the first measurement liquid is fed, via the fine flow channel, in such a manner that the first measurement liquid does not reach the liquid-mixing section arranged on the downstream side of the fine flow channel.

16. The antigen detection method according to claim 15, further comprising:
a second reaction washing step including washing the reaction zone with a second washing liquid after the second reaction step,
wherein in the second reaction washing step, the second washing liquid is fed, via the fine flow channel, in such a manner that the second washing liquid does not reach the liquid-mixing section arranged on the downstream side of the fine flow channel.

17. The antigen detection method according to claim 16, further comprising:

a second reaction measurement liquid-filling step including filling the reaction zone with a second measurement liquid after the second reaction washing step, wherein in the second reaction measurement liquid-filling step, the second measurement liquid is fed in such a manner that the measurement liquid does not reach the liquid-mixing section arranged on the downstream side of the fine flow channel.

18. The antigen detection method according to claim 17, wherein:

the signal measurement step is performed a first time while the reaction zone is filled with the first measurement liquid in the first reaction measurement liquid-filling step, and the signal measurement step is performed a second time while the reaction zone is filled with the second measurement liquid in the second reaction measurement liquid-filling step.

19. The antigen detection method according to claim 18, further comprising:

obtaining a measurement value based on the target antigen using (i) a result of the signal measurement step performed while the reaction zone is filled with the first measurement liquid in the first reaction measurement liquid-filling step, and (ii) a result of the signal measurement step performed while the reaction zone is filled with the second measurement liquid in the second reaction measurement liquid-filling step.

* * * * *